(12) United States Patent
Carrel et al.

(10) Patent No.: US 8,308,687 B2
(45) Date of Patent: Nov. 13, 2012

(54) INJECTION SET AND INJECTION ASSISTANCE DEVICE

(75) Inventors: Franck Carrel, Pont de Claix (FR); Frederic Perot, Saint Paul de Varces (FR); Jean-Pierre Grimard, Vif (FR)

(73) Assignee: Becton Dickinson France (FR)

( * ) Notice: Subject to any disclaimer, the term of this patent is extended or adjusted under 35 U.S.C. 154(b) by 67 days.

(21) Appl. No.: 11/912,270

(22) PCT Filed: Apr. 20, 2006

(86) PCT No.: PCT/IB2006/001740
§ 371 (c)(1),
(2), (4) Date: Jun. 9, 2009

(87) PCT Pub. No.: WO2006/129196
PCT Pub. Date: Dec. 7, 2006

(65) Prior Publication Data
US 2009/0318864 A1   Dec. 24, 2009

(30) Foreign Application Priority Data
Apr. 20, 2005   (FR) .................................. 05 03963

(51) Int. Cl.
*A61M 5/20* (2006.01)

(52) U.S. Cl. ........................................ 604/136

(58) Field of Classification Search ............... 604/117, 604/110, 197, 135, 136, 131, 157, 165.01, 604/165.02, 240
See application file for complete search history.

(56) References Cited

U.S. PATENT DOCUMENTS

| | | |
|---|---|---|
| 3,702,608 A | 11/1972 | Tibbs |
| 5,267,963 A | 12/1993 | Bachynsky |
| 5,320,609 A | 6/1994 | Haber et al. |
| 5,478,316 A * | 12/1995 | Bitdinger et al. ............. 604/135 |

FOREIGN PATENT DOCUMENTS

EP   0 666 084 A2   1/1995

* cited by examiner

Primary Examiner — Nicholas Lucchesi
Assistant Examiner — Brooke Matney
(74) Attorney, Agent, or Firm — Hoffmann & Baron, LLP

(57) ABSTRACT

The present invention relates to an injection assistance device (1) for an injection device (3) comprising one body (2), one needle (7), and one piston plunger (26), characterized in that it comprises: a hollow sleeve (4) receiving the body (2), coupling arrangement (10) for moving the piston plunger (26) from an end-of-insertion position to an end of injection position the coupling arrangement being maintained in a passive state until the end-of-insertion position, spacer arrangement (8) to maintain the piston plunger (26) and the body (2) in an initial position, disengaging arrangement (22, 14, 15, 16) linked with the spacer arrangement (8), the spacer arrangement (8) and/or disengaging arrangement (22, 14, 15, 16; 25, 31) being arranged in order not to free the distal displacement of the piston plunger (26) before the one of the body (2).

20 Claims, 12 Drawing Sheets

Figure 1:
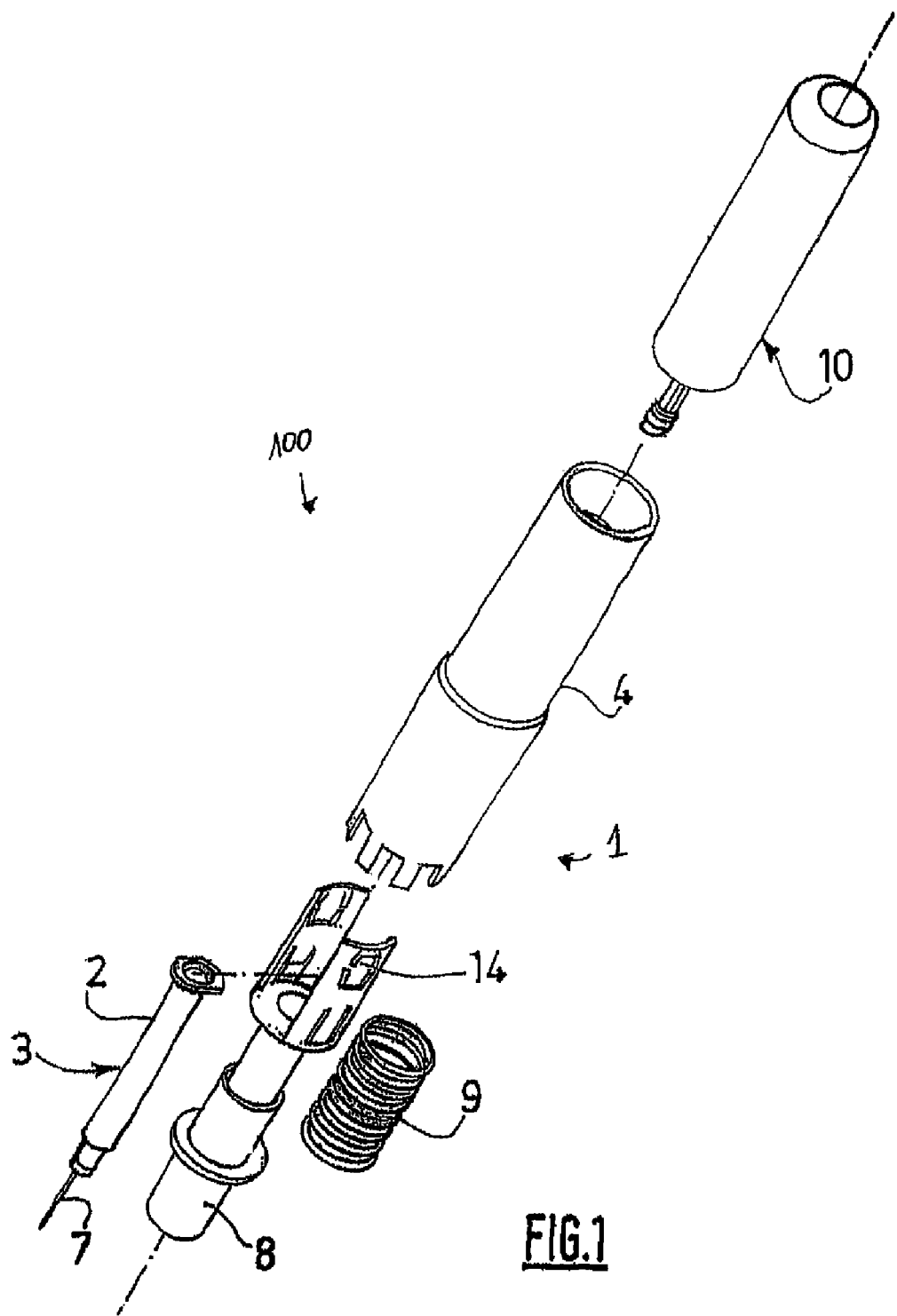

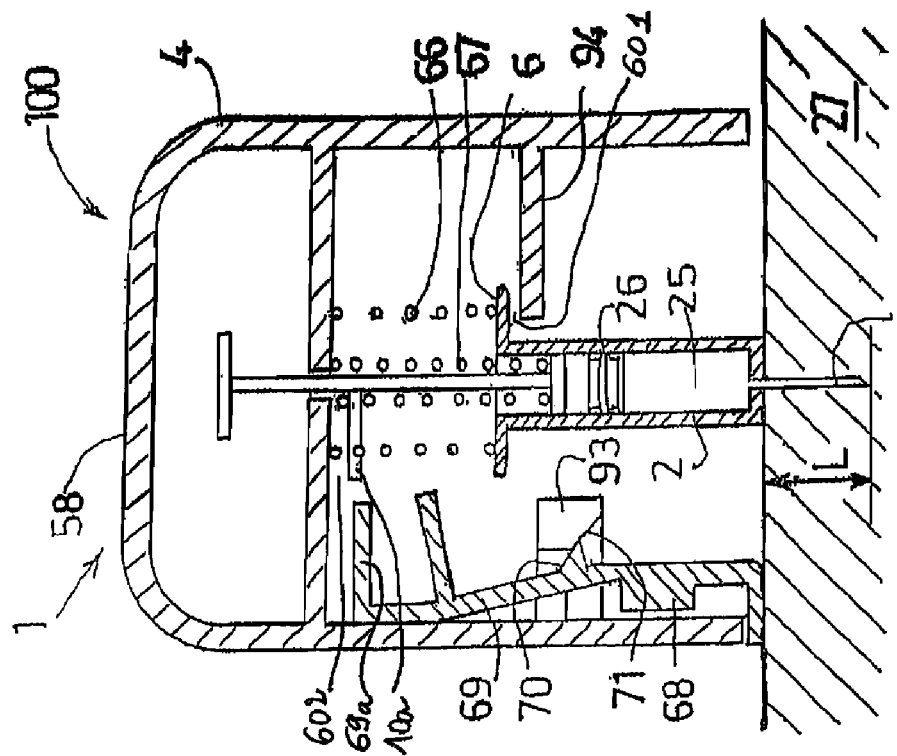
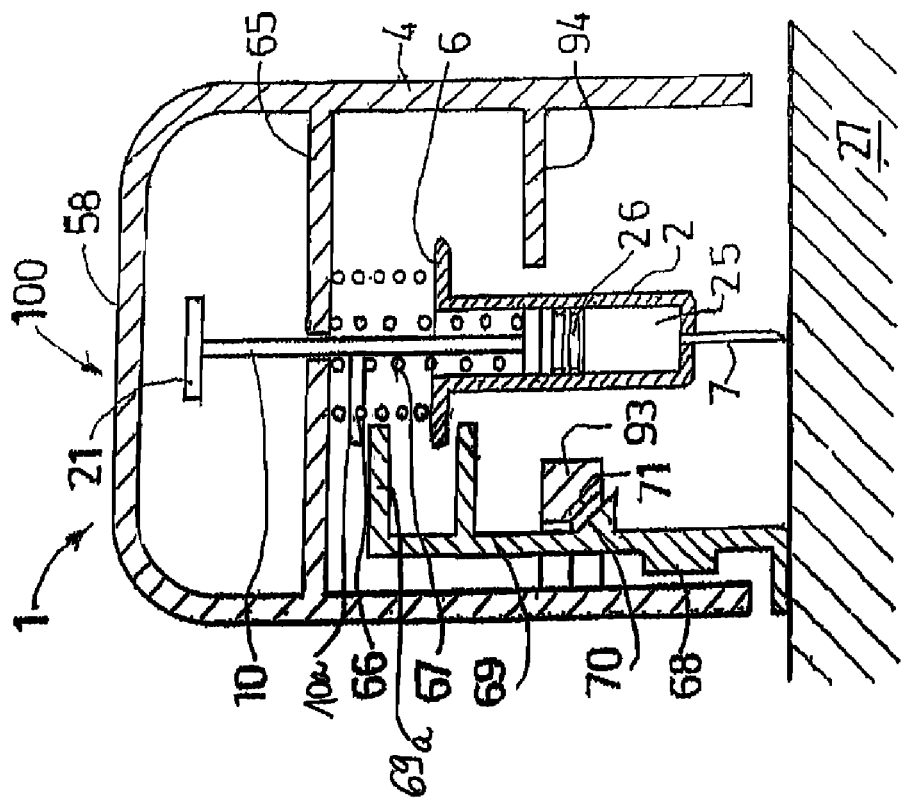

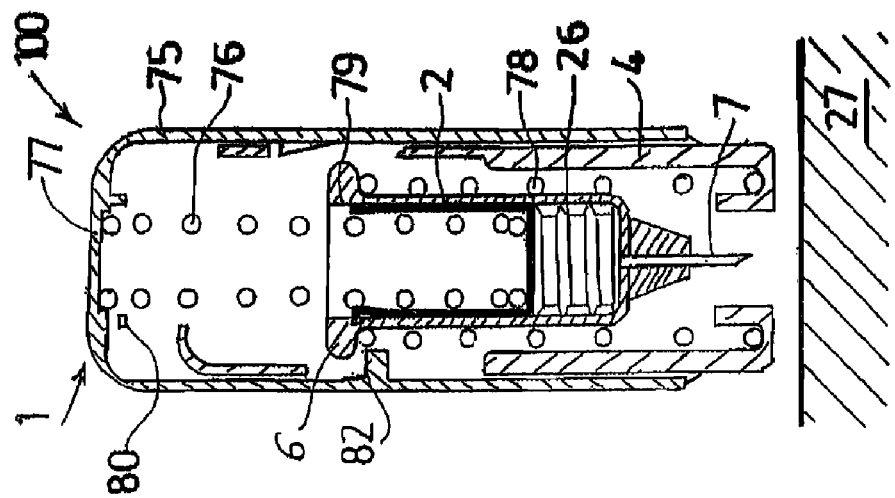
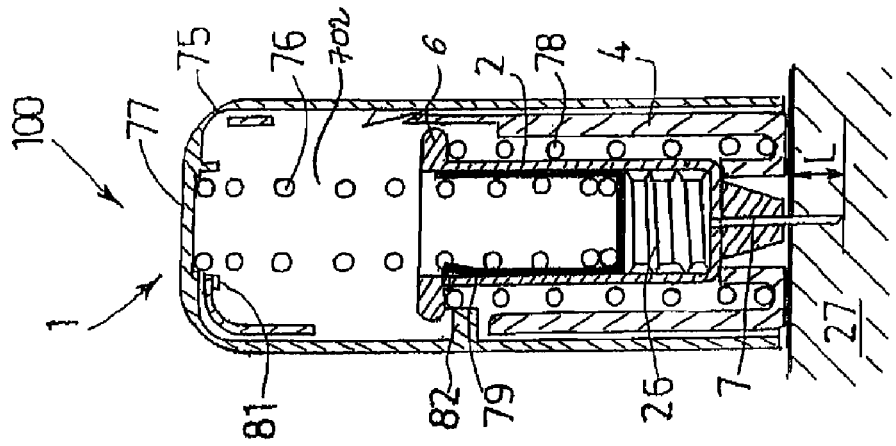
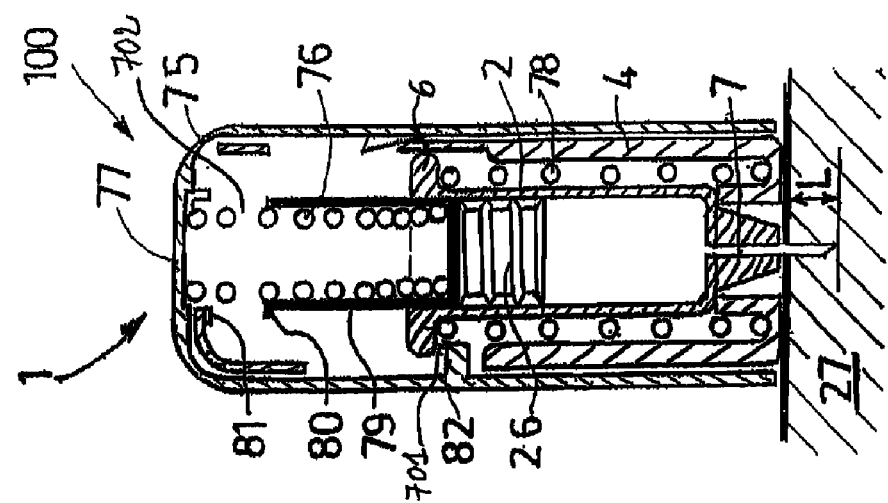

INJECTION SET AND INJECTION ASSISTANCE DEVICE

The present invention relates to an injection assistance device for an injection device and to an injection set provided with the said injection assistance device, these devices allowing a product to be injected into an injection site.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

In order to administer a medicinal product to a body, particularly the human body, there are various possible routes depending on the place in the body at which the said product is to be injected: thus, the product may be injected intravenously, intramuscularly, subcutaneously, into a joint, or else intradermally. In many of these latter cases, and, particularly when injecting subcutaneously, the depth to which the needle is inserted and therefore at which the product is injected is particularly significant. Thus, it is possible to observe an adverse immunological reaction if, for example, a product that should have been injected into the subcutaneous tissues is finally injected into the intradermal tissues.

The operation of injecting a product using a syringe is particularly delicate. The patient may make an unforeseen movement or alternatively the person administering the injection might make a wrong move. Thus, errors in the depth to which the needle is inserted are particularly difficult to avoid and discrepancies of just a few millimeters may, themselves alone, lead to errors in injection depth.

Likewise, once the needle has been inserted, it is important to guarantee that this insertion depth is maintained throughout the injecting of the product so as to guarantee the correct injection depth.

As far as subcutaneous injection is concerned, there are various injection techniques currently used. Some users prefer to pinch the skin before inserting the needles, others prefer not to, and still others angle the syringe before inserting it into the skin, it being possible for this angle to vary from one user to another. The result of all this is that the depth to which the needle is inserted and therefore at which the product is injected may itself also vary, with the unpleasant consequences mentioned above.

Furthermore, in this kind of operation, it is also important to avoid any needlestick injury due to the exposed needle, whether this be before or after injection.

In addition, to limit the apprehension felt by the patient, particularly in the case of injections administered by the patient himself, it is desirable for the injection device not to look like a conventional syringe and/or for the needle not to be visible or to be visible only a little prior to insertion.

Finally, injecting a product using traditional injection devices generally entails at least two manual steps. For example, in the case of syringes, one manual step is to hold the body of the syringe in order to insert the needle into the injection site, another step consists in pressing on the plunger rod in order to administer the injection, the progression from one step to the other generally entailing moving the fingers with respect to the syringe.

Document EP 0 666 084 A2 discloses an automatic injection device for automatically injecting a material into the body.

There therefore remains a need for an injection assistance device and for an injection set which are made safe, that is to say which make it possible to limit the impact of undesired movements of the patient and/or of the user in order to prevent a variation in the depth to which the needle is inserted when administering the injection so as to avoid unintentionally injecting the said product at an inadequate depth, limiting the number of manipulations to be carried out by the user, limiting the risk of needlestick injury both to the patient and to the person performing the injection, limiting the apprehension felt by the patient and making the giving of the injection easier.

There also remains a need for such an injection assistance device and an injection set that allow the user to be certain of causing the needle to penetrate the injection site to a predetermined insertion depth and, in addition, guarantee that the injection is administered at this predetermined depth.

There also remains a need for such an injection assistance device and an injection set that ensure that the injection is not triggered before the needle is inserted at the right insertion depth.

The present invention remedies these needs by proposing an injection assistance device for an injection device for injecting a product into an injection site, this injection device comprising at least one hollow body intended to receive a product that is to be injected, at least one hollow injection needle intended to penetrate the injection site, and at least one piston plunger housed in the said body, the said body and the said piston plunger being able to be moved in axial translation one with respect to the other, characterized in that the said injection assistance device comprises at least:
  a hollow sleeve provided with at least one bearing surface intended to come into contact with the surface of the said injection site, the said sleeve being intended to receive, at least in part, the said body and being arranged in such a way as to allow the said body axial mobility between at least a first position known as the initial position in which the said needle is not exposed over its insertion length, and a second position known as the insertion position in which the said needle is exposed by a predetermined insertion length L,
  coupling means arranged in such a way as to be coupled to said piston plunger at least during an injection step so as to move said piston plunger from an end-of-insertion position to an end of injection position and to administer the injection when submitted to a distal pressure exerted on them,
  spacer means arranged in such a way as to maintain at least said piston plunger and said body in said initial position,
  disengaging means linked with said spacer means, said spacer means and/or disengaging means being arranged in order not to free the distal displacement of said piston plunger before the one of said body.

In a preferred embodiment of the invention, the injection assistance device further comprises:
  automatic-insertion means arranged in such a way as to cause the said body to move axially in the distal direction and to insert the said hollow needle into the injection site,
  retaining means for retaining the said body in the said initial position, the said automatic-insertion means being activated by the release of the said retaining means.

By "spacer means", is meant, in the present application means to prevent from moving said piston plunger before moving said body so as to not perform the injection before reaching the insertion position, even if distal pressure is exerted on said coupling means: said coupling means may be prevented from enabling said piston plunger displacement either because they are rigidly connecting the plunger piston to said body during the insertion step or because they are released at the same time as said piston plunger and said body.

The injection assistance device according to the invention allows the injection to be administered in a minimum number of actions, particularly disposing with at least one of the two manual steps described hereinabove, and preferably dispensing with these two manual steps. Thus, the operation of administering the injection is entirely safe, the step of inserting the needle in particular being done automatically, without the user having to intervene. Any risk of error is thus avoided.

In an embodiment of the invention, the said coupling means comprise at least one plunger rod detached from the said piston plunger, the said plunger rod being able, once coupled to said piston plunger, to drive the said piston plunger in the distal direction when urged in the distal direction.

In an embodiment of the invention, said spacer means comprise at least one spacer forming a substantially rigid link between said body and said piston plunger and preventing their relative displacement before the triggering of said disengaging means.

Advantageously, said disengaging means are arranged in order to automatically disengage said spacer when the insertion position is reached and free the relative displacement of said piston plunger and said body.

In an embodiment of the invention, the injection assistance device further comprises automatic-injection means arranged in such a way as to urge the said coupling means at the end of the insertion position without manual intervention on the part of the user.

In an embodiment of the invention, said automatic-injection means comprise first return means connected to the said coupling means and intended to urge the said coupling means from the insertion position to the said end-of-injection position.

In an embodiment of the invention, the injection assistance device comprises maintaining means for keeping the said coupling means in the said insertion position, the said automatic-injection means being activated by the release of the said maintaining means.

In a preferred embodiment, said disengaging means are triggered by the release of the said maintaining means to simultaneously perform the disengagement of said spacer and the activation of said automatic-injection means.

In an embodiment of the invention, with the said body comprising a flange at its proximal end, the said maintaining means comprise at least one deflecting tab engaging the said body and the said coupling means in the insertion position, the said tab being able to deflect and to disengage the said body from the said coupling means by collaborating with the said flange at the end of the insertion position.

In an embodiment of the invention, the injection assistance device further comprises final protection means arranged in such a way as to cover the said needle in a post-injection final protection position, which means are able to move in translation with respect to the said body between an injection position in which the needle is exposed and a final protection position in which the needle is covered.

In an embodiment of the invention, the final protection means are chosen from the said sleeve and an intermediate sheath arranged between the said sleeve and the said body.

In an embodiment of the invention, the injection assistance device comprises automatic-activation means for activating the said final protection means at the end of injection.

In an embodiment of the invention, the automatic activation means comprise second return means connected to the said final protection means intended to urge the said body from the said injection position to the said final protection position.

In an embodiment of the invention, the injection assistance device comprises locking means arranged in such a way as to at least limit the translational movement of the said body with respect to the said final protection means in the final protection position.

In an embodiment of the invention, the said automatic-insertion means comprise third elastic return means connected to the said sleeve and intended to urge the said body from the initial position to the said insertion position.

In an embodiment of the invention, the said piston plunger having a force needed to overcome the stiction of the hollow body, the said automatic-injection means are activated when the resultant of the forces of the said first, second and third return means, the resisting force of the said piston plunger and the bearing force of the sleeve on the said injection site is directed in the distal direction.

In an embodiment of the invention, the injection assistance device comprises control means arranged in such a way as to delimit the said insertion position of the said body.

In an embodiment of the invention, the said control means comprise at least one radial stop provided in the said sleeve and intended to have the said body bearing against it.

In an embodiment of the invention, wherein the said piston plunger is connected to a plunger rod intended to urge the said piston plunger in the distal direction in order to perform the injection, the said control means comprise blocking means for blocking the translational movement of the said plunger rod with respect to the said piston plunger, the said blocking means being able to be released when the said body is at the end of the insertion position, the said needle being exposed by the said predetermined insertion length L.

The present invention also relates to an injection set for injecting a product into an injection site, the said injection set comprising at least:
  an injection device comprising at least:
    a hollow body intended to receive a product that is to be injected, the said body being equipped with a hollow injection needle intended, during a first step known as the insertion step, to penetrate an injection site and, during a second step known as the injection step, to channel the said product from the said body towards the said injection site,
    at least one piston plunger housed in a more or less sealed manner in the said body and intended to be moved in the distal direction by movement means in the said injection step during which it drives the said product through the said needle,
characterized in that it comprises at least an injection assistance device for assisting with the injection device as described hereinabove.

In one embodiment of the invention, the injection set is in the form of a kit that can be assembled prior to use.

Figure 17:
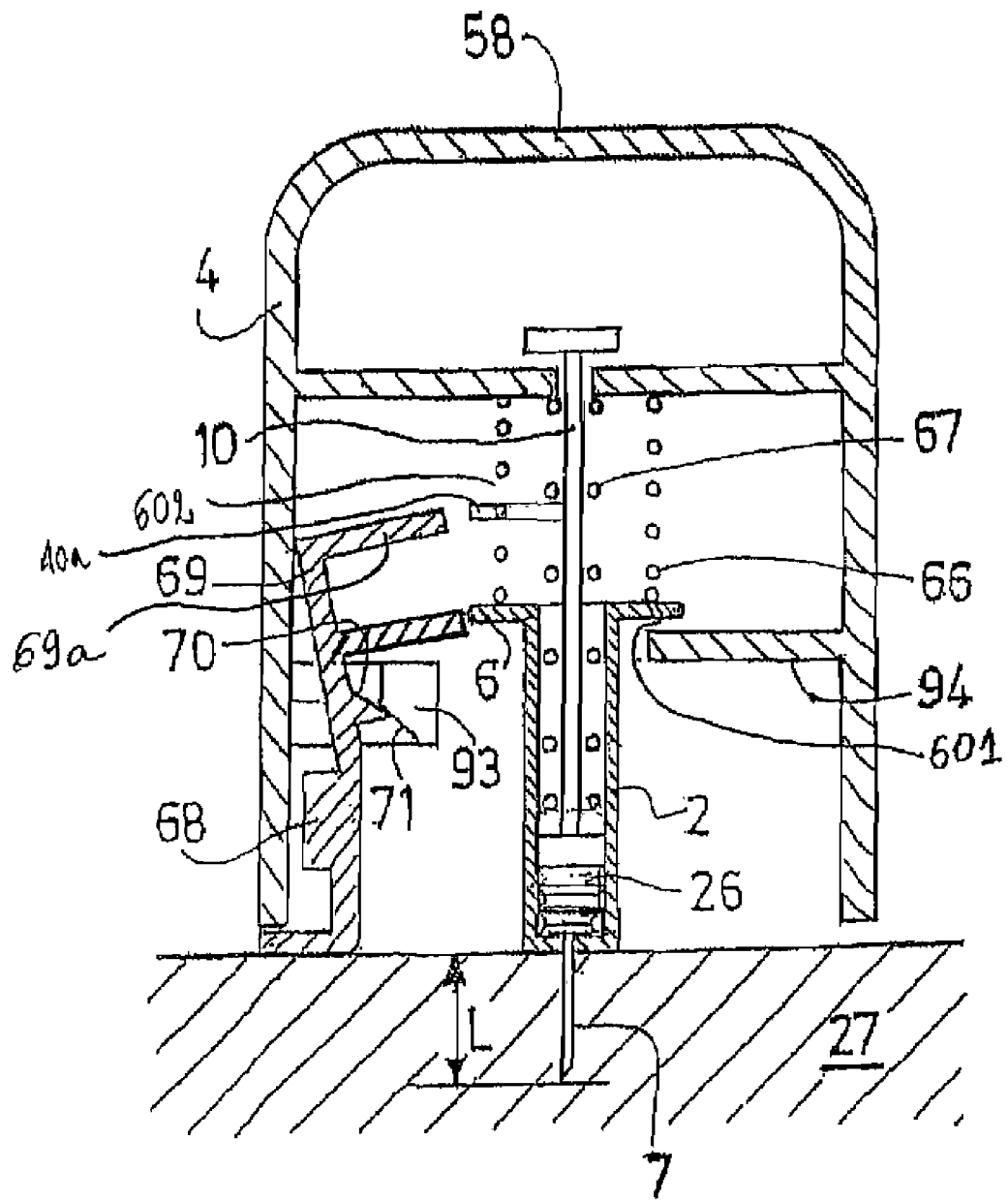

Other advantages and alternative forms of the present invention will be specified with the aid of the description which will follow and of the attached drawings in which:

FIG. 1 is an exploded perspective view of an injection set according to the invention, FIGS. 2 to 5 are simplified sectioned views of the injection set of FIG. 1 in the following respective positions: initial, insertion, end-of-injection, final protection, FIGS. 6 to 10 are sectioned views of a first alternative form of embodiment of an injection set according to the invention in the following respective positions: initial, insertion, end-of-injection before triggering of safety, triggering of safety, final protection, FIGS. 11 to 14 are sectioned views of a second alternative form of embodiment of an injection set according to the invention, in the following respective positions: initial, insertion, end-of-injection, final protection, FIGS. 15 to 17 are sectioned views of a third alternative form of embodiment of an injection set according to the invention in the following respective positions: initial, insertion, end-of-injection, FIGS. 18 to 22 are sectioned views of a fourth alternative form of embodiment of an injection set according to the invention in the following respective positions: initial, pre-insertion, insertion and start-of-injection, end-of-injection, final protection.

In order to make the invention easier to understand, the injection assistance device is described assembled with an injection device with which it forms an injection set.

FIG. 1 depicts an injection set 100 according to the invention, comprising an injection assistance device 1 for an injection device 3, this injection device 3 comprising a hollow body 2 intended to receive a product 25 that is to be injected, at least one hollow injection needle 7 intended to penetrate the injection site 27, and at least one piston plunger 26 housed in the said body 2, the said body 2 and the said piston plunger 26 being able to be moved in axial translation one relative to the other as will be visible from FIGS. 2 to 5. The body 2 also comprises a flange 6 at its proximal end.

Figure 2:
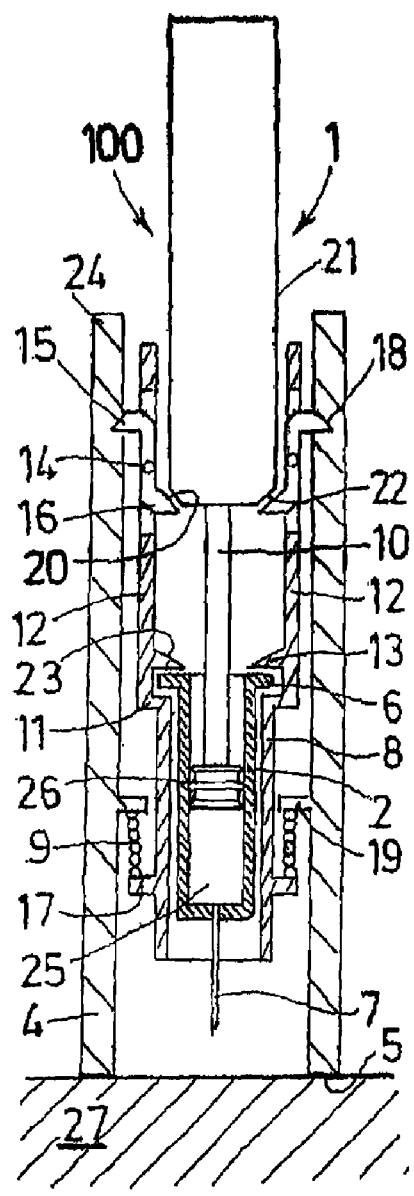
Figure 3:
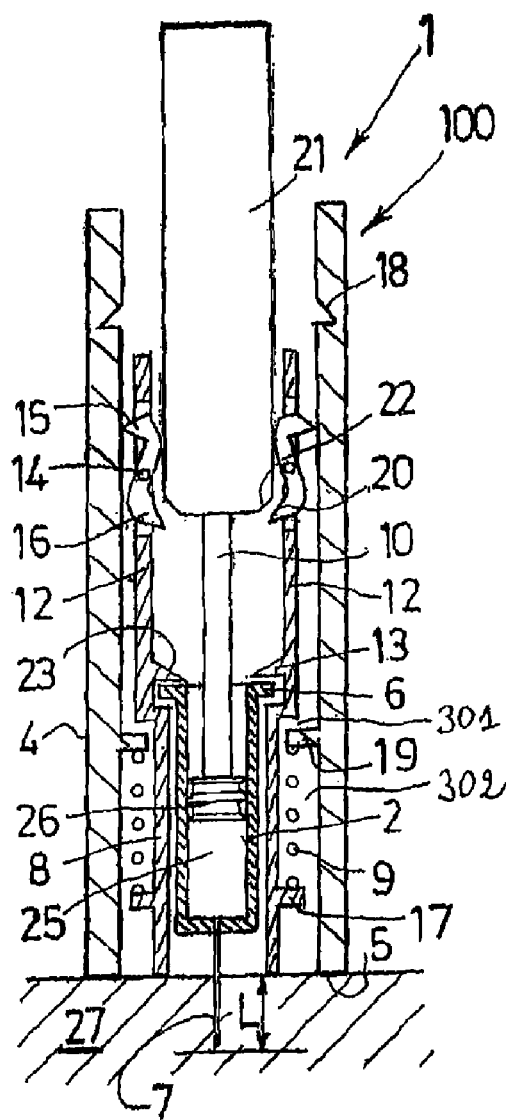
Figure 4:
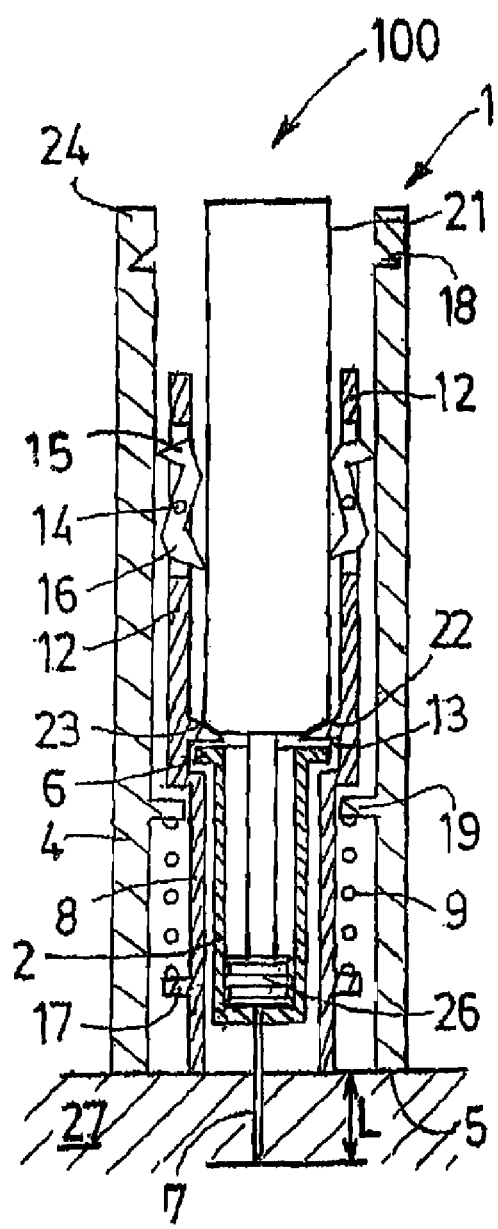

The injection assistance device 1 of FIGS. 1 to 5 comprises a hollow sleeve 4 which at least partially houses the said body 2, this sleeve 4 being provided with at least one bearing surface 5 intended to come into contact with the surface of the injection site 27 as shown in FIGS. 2 to 4.

The injection assistance device 1 also comprises an intermediate ring 8 attached to the flange 6 of the body 2, a spring 9, arranged between the said sleeve 4 and the said intermediate ring 8, and a plunger rod 10 intended to be coupled to the piston plunger 26 in order to administer to inject the product 25.

The plunger rod 10 is equipped with a head 21 the distal end of which is equipped with an external ramp 22.

At its proximal end the intermediate ring 8 comprises at least an external radial rim 11 from which two diametrically opposed tabs 12 extend in the proximal direction, each tab 12 being equipped on its internal wall and in its distal part with at least one internal radial projection 13 able to deflect radially outwards, each tab 12 further comprising, formed in the wall of its proximal part, at least one tab 14 comprising an external radial proximal tooth 15 and an internal radial distal tooth 16, each of the said proximal 15 and distal 16 teeth being able to deflect radially in such a way that the outwards radial flexing of the said distal tooth 16 causes the inwards radial flexing of the said proximal tooth 15.

The distal tooth 16 is equipped with an inclined proximal face 20. The internal radial projection 13 comprises a sloping proximal face 23.

The intermediate ring 8 further comprises at least one external radial stop 17 formed on the external wall of its distal part.

The sleeve 4 comprises at least one notch 18 formed on the internal wall of its proximal part and an internal radial step 19 situated on the internal wall of its distal part.

As can be seen from FIGS. 2 to 5, the proximal end of the spring 9 bears against the distal face of the said radial step 19 and the distal end of the spring 9 bears against the proximal face of the said radial stop 17.

The injection assistance device 1, into which the injection device 3 is integrated, is supplied in the initial position shown in FIG. 2. In this position, the flange 6 of the body 2 is clipped between the said external radial rim 11 and the said internal radial projection 13. The spring 9 is compressed and the said proximal tooth 15 is engaged in the said notch 18 so as to block the translational movement of the said intermediate ring 8 with respect to the said sleeve 4. The sleeve 4 entirely covers the hollow needle 7 and the injection assistance device 1 is therefore completely safe.

In order to proceed with the injection, the user grasps hold of the sleeve 4 via a proximal region for holding 24 and places it bearing, via its bearing surface 5, against the surface of the injection site 27.

The user then engages the plunger rod 10 inside the sleeve 4 in the axial direction. During this movement, the said external ramp 22 comes into contact with the said inclined proximal face 20 causing the said distal tooth 16 to flex outwards and therefore causing the said proximal tooth 15 to flex inwards, the said proximal tooth 15 disengaging from the said notch 18 and releasing the said intermediate ring 8 which is moved in the distal direction by the deployment of the said spring 9. As the intermediate ring 8 is also fixed to the said collar 6, it carries with it the said hollow body 2 and therefore the said needle 7 which penetrates the injection site 27 as shown in FIG. 3. Thus, insertion of the needle 7 into the injection site 27 is performed automatically, without the user having to move the said body 2 by hand.

As can be seen from FIG. 3, the needle 7 has penetrated the injection site 27 to a predetermined insertion length L controlled by the distal end of the said intermediate ring 8 coming into abutment against the surface of the injection site 27 and the thrusting of the said spring 9 in the partially expanded state against the said radial stop 17. In this insertion position, the axial gap 301 left between the intermediate ring 8 and the sleeve 4 allows the needle 7 to be kept at the insertion depth L even if the user moves the hand holding the sleeve slightly away from the injection site 27.

Actually, if during the injection step, the user, for instance by inadvertence, releases the distal pressure he exerts on the sleeve 4 when applying it on the injection site 27, causing thereby a limited proximal movement of said sleeve 4, then the spring 9, because it is in a partially expanded state and thanks to the presence of the gap 301, is allowed to dampen said proximal movement by expanding a little more and thereby causing the intermediate ring 8 to be urged towards the injection site 27. The body 2 being coupled to said intermediate ring 8, it is also urged towards the injection site 27 and the needle 7 is maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 9, because it is in a partially expanded state and thanks to the presence of the space 302 between the radial step 19 of the sleeve 4 and the radial stop 17 of the intermediate ring 8, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 9 in a partially expanded state.

During the insertion step that has been described, the plunger rod 10 was not released by the retaining means before the body 2. In consequence, there is limited risk that the injection be started before the needle is inserted at the right insertion depth L.

In addition, in an embodiment not depicted, the injection assistance device 1 can be arranged in order to allow sequential displacement of, in a first step the body 2 and the plunger rod 10 relative to the sleeve 4 and in a second step of the plunger rod 10 relative to said body 2. To do so, internal radial distal teeth 16 and said proximal 15 teeth are arranged in order to, when the user engages the plunger rod 10 inside the sleeve 4 in the axial direction, first allow the disengagement of the internal radial distal teeth 16 and said proximal 15 teeth in two separate steps, a first step during which, proximal .15 teeth are disengaged from notch 18 to allow insertion of the needle 7 with no relative displacement of the plunger rod 10, and a second step in which, when the intermediate ring 8 is in abutment with the injection site 27, the distal 16 teeth are disengaged from the external ramp 22 of the piston rod 10 to allow displacement of the plunger rod 10 relative to the body 2 and allow the injection of the product 25 in the injection site 27. In consequence, there is no risk that the injection be started before the needle is inserted at the right insertion depth L.

In order to actually perform the injection, the user, still keeping the injection assistance device 1 pressed against the injection site 27, grasps hold of the plunger rod 10 and couples it to the said piston plunger 26 so as to move the said piston plunger 26 in the distal direction. The said piston plunger 26 then drives the product 25 towards the needle 7, and the injection is performed.

At the end of injection, as shown in FIG. 4, the said external ramp 22 comes into contact with the said sloping proximal face 23 and, under the effect of an axial force exerted on the head 21 of the plunger rod 10, causes the said radial projection 13 to flex radially outwards thus disengaging the said flange 6 from the said intermediate ring 8.

Figure 5:
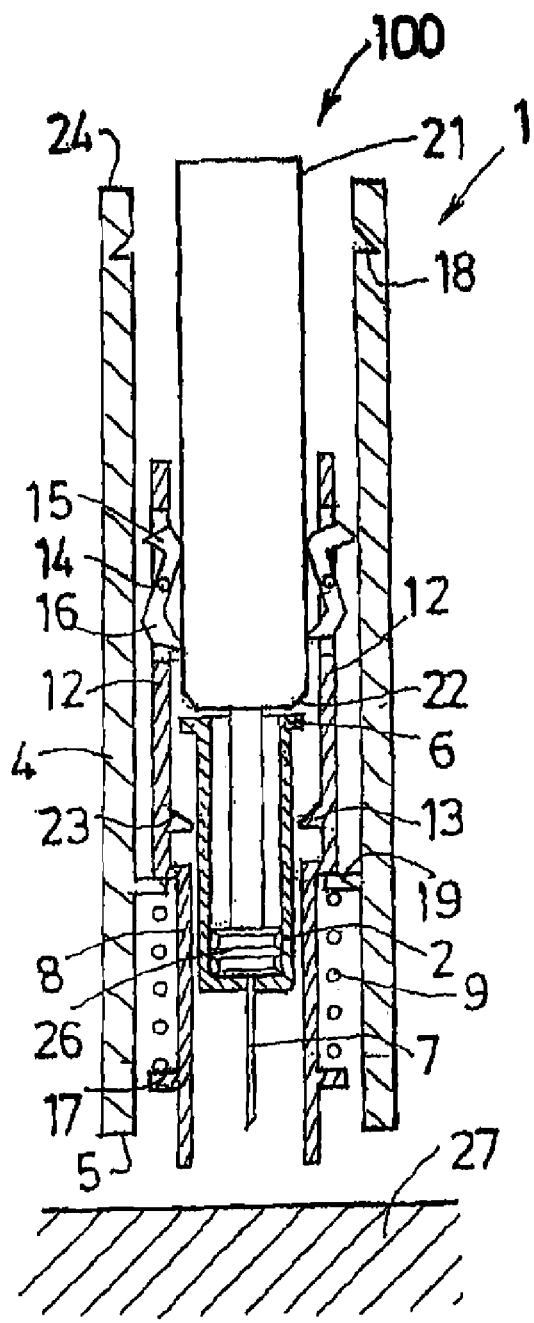

The user then withdraws the injection assistance device 1 from the surface of the injection site 27 and the spring 9, relieved of the pressure exerted on it by the said surface of the said injection site 27, returns to its expanded state, carrying with it the said intermediate ring 8, of which the distal part covers the needle 7 as shown in FIG. 5.

The said radial stop 17 then comes into abutment against the bearing surface 5 of the said sleeve 4, thus locking the translational movement of the said sleeve 4 with respect to the intermediate ring 8.

Thus, the injection assistance device 1 is completely safe and the user can discard it without the risk of needlestick injury.

In an embodiment, not depicted, of the invention, insertion of the needle is triggered by a rotation of the said intermediate ring with respect to the said plunger rod.

FIGS. 6 to 10 illustrate a first alternative form of embodiment of the injection set 100 according to the invention. Identical references have been maintained.

The injection set 100 of FIGS. 6 to 10 comprises an injection assistance device 1 for an injection device 3, this injection device 3 comprising a hollow body 2 intended to receive a product 25 that is to be injected, at least one hollow injection needle 7 intended to penetrate the injection site 27, and at least one piston plunger 26 housed in the said body 2. The body 2 also has a flange 6 at its proximal end.

Figure 6:
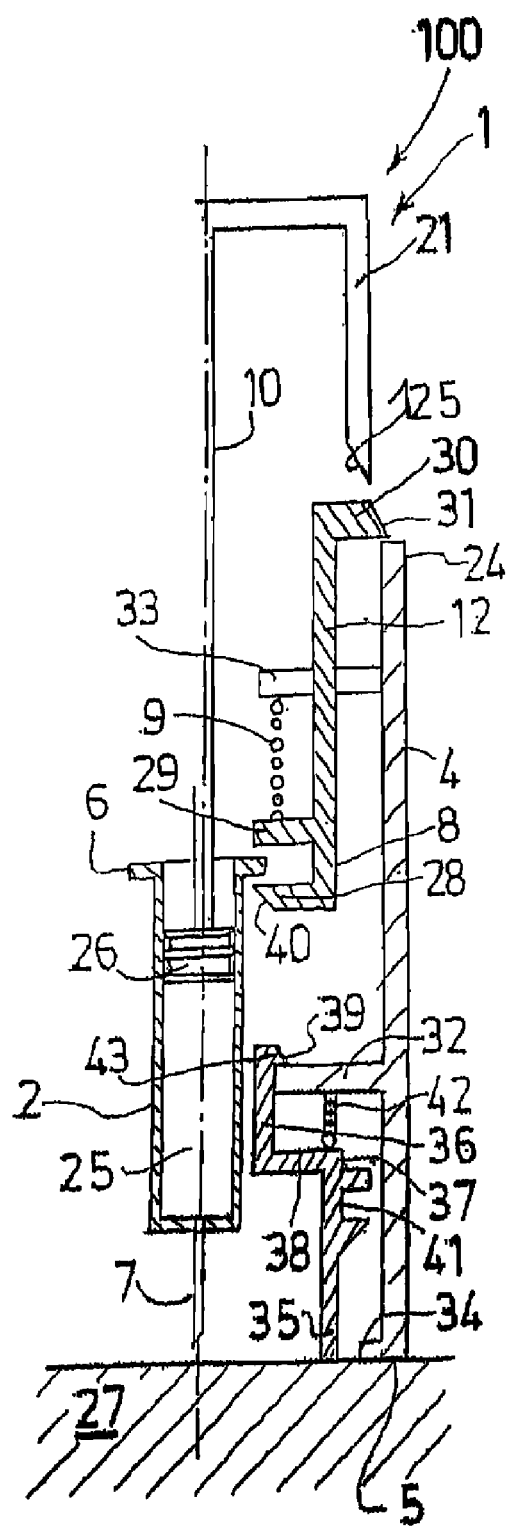
Figure 7:
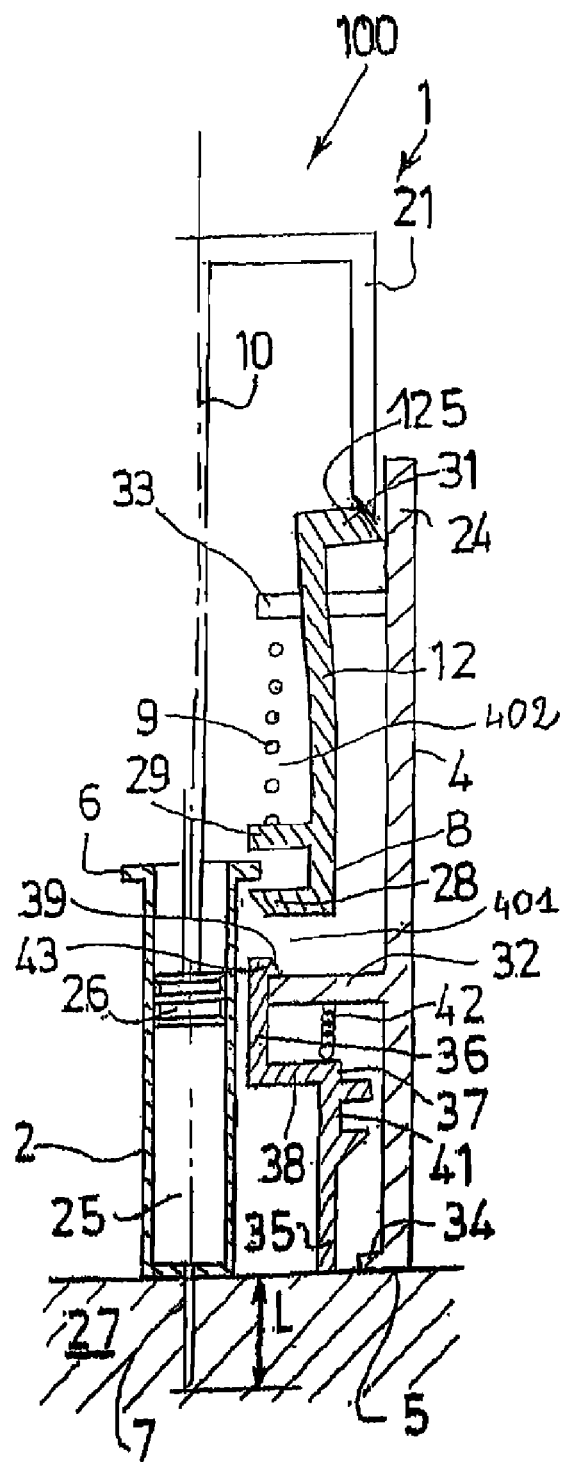
Figure 8:
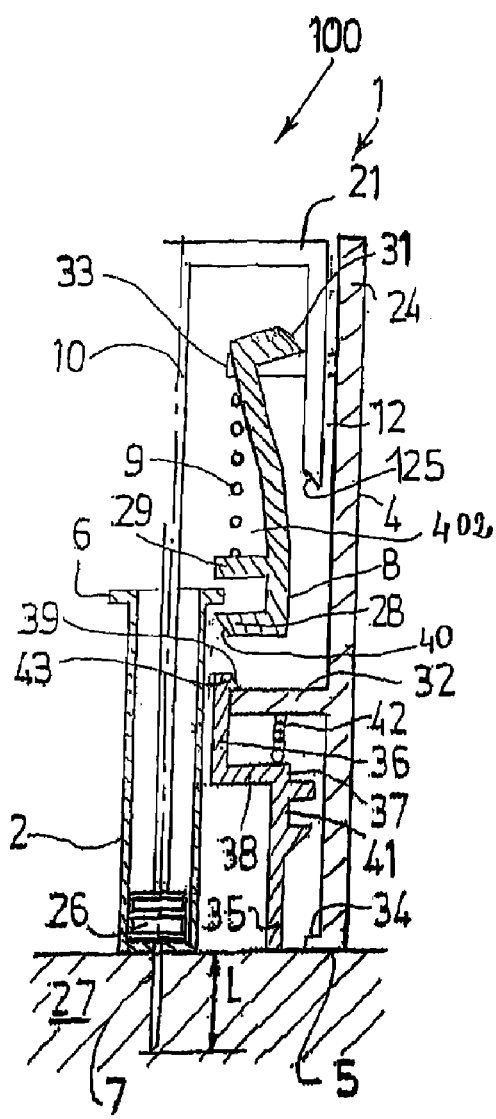

The injection assistance device 1 of FIGS. 6 to 10 comprises a hollow sleeve 4 which at least partially houses the said body 2, this sleeve 4 being provided with at least one bearing surface 5 intended to come into contact with the surface of the injection site 27 as shown in FIGS. 6 to 8.

The injection assistance device 1 also comprises an intermediate ring 8 attached to the flange 6 of the hollow body 2, a first spring 9 arranged between the said sleeve 4 and the said intermediate ring 8, and a plunger rod 10 intended to be coupled to the piston plunger 26 in order to perform the injection.

The plunger rod 10 is equipped with a head 21 forming a longitudinal skirt of which the distal end is equipped with an internal ramp 125.

The said intermediate ring 8 comprises a distal tooth 28, a proximal tooth 29 and at least two diametrically opposed tabs 12 each one extending in the proximal direction from the proximal face of the said proximal tooth 29, each tab 12 being equipped at its proximal end with an external radial projection 30 able to deflect radially inwards. The said external radial projection 30 comprises an inclined proximal face 31. The said distal tooth 28 also comprises an inclined distal face 40.

In FIGS. 6 to 10, the sleeve 4 comprises a proximal part and a distal part separated from one another by an internal radial rim 32. The proximal part of the said sleeve 4 is equipped with an internal radial stop 33 and the distal part of the said sleeve 4 is equipped with an internal bulge 34.

In its distal part, the said sleeve 4 accommodates a sheath 35 comprising a tubular proximal part 36 and a tubular distal part 37, the diameter of the cross section of the proximal part 36 being smaller than the diameter of the cross section of the distal part 37, the said proximal 36 and distal 37 parts being connected to one another by a transverse wall 38 in the form of a circular band, the said proximal part 36 being equipped at its proximal end with an external radial step 43 able to deflect radially inwards. The said external radial step 43 is equipped with a sloping proximal face 39. The said sheath 35 also comprises a slot 41 formed on the external wall of its tubular distal part 37.

The injection assistance device 1 of FIGS. 6 to 10 also comprises a second spring 42 arranged between the said sheath 35 and the distal part of the said sleeve 4.

In the initial position depicted in FIG. 6, the said first spring 9 is in the compressed state and its distal end bears against the proximal face of the said proximal tooth 29, while its proximal end bears against the distal face of the said radial stop 33. In this position, the said second spring 42 is also in the compressed state and its distal end bears against the proximal face of the said transverse wall 38 of the said sheath 35 whereas its proximal end bears against the distal face of the said internal radial rim 32.

The intermediate ring 8 is clipped onto the flange 6 of the hollow body 2 by means of its distal 28 and proximal 29 teeth. The said external radial projection 30 is in abutment against the proximal end 24 of the said sleeve 4, blocking the translational movement of the said hollow body 2 with respect to the said sleeve 4. The distal face of the said radial step 39 is in abutment against the proximal face of the said radial rim 32, blocking the translational movement of the said sleeve 4 with respect to the said sheath 35.

In the initial position depicted in FIG. 6, the said sleeve 4 and the said sheath 35 completely cover the needle 7. The injection assistance device 1 is therefore completely safe.

In order to proceed with the administering of the product 25, the user grasps hold of the sleeve 4 via its proximal end 24, forming a proximal region for holding of the said sleeve 4, and places it bearing, via its bearing surface 5, against the surface of the injection site 27.

The user then engages the plunger rod 10 inside the sleeve 4 in the distal direction. During this movement, the said internal ramp 125 comes into contact with the said inclined proximal face 31 causing the said external radial projection 30 to flex and disengage from the said sleeve 4 and release the said intermediate ring 8, the latter being moved in the distal direction, by the deployment of the said first spring 9 which returns to a partially expanded state. As the intermediate ring 8 is also fixed to the said flange 6, it carries with it the said hollow body 2 and therefore the said needle 7 which penetrates the injection site 27 as shown in FIG. 7.

As can be seen in FIG. 7, the needle 7 has penetrated the injection site 27 to a predetermined insertion length L controlled by the distal face of the said intermediate ring 8 coming into abutment against the proximal face of the said radial rim 32 and by the thrusting of the said first spring 9 in the partially expanded state against the proximal face of the proximal tooth 29 of the said intermediate ring 8.

In the insertion position shown on FIG. 7, a gap 401 is left between the distal tooth 28 of the intermediate ring 8 and the internal radial rim 32 of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 9, because it is in a partially expanded state and thanks to the presence of the gap 401, is allowed to dampen said proximal movement by expanding a little more and thereby causing the intermediate ring 8 to be urged towards the injection site 27. The body 2 being coupled to said intermediate ring 8, it is also urged towards the injection site 27 and the needle 7 is maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 9, because it is in a partially expanded state and thanks to the presence of the space 402 between the radial stop 33 of the sleeve 4 and the proximal tooth 29 of the intermediate ring 8, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 9 in a partially expanded state.

During the insertion step that has been described, the intermediate ring 8 is forming a spacer that rigidly connects, during the insertion step, the plunger rod 10 to the body 2. There was therefore no risk that the injection be started before the needle 7 was inserted at the right insertion depth L.

In order to actually administer the product 25, the user, still holding the injection assistance device 1 against the injection site 27, grasps hold of the plunger rod 10 and moves it in the distal direction. During this movement, the said internal ramp 125 in contact with the said inclined proximal face 31 causes the said external radial projection 30 to flex and disengage from the said head 21 of the plunger rod 10, enabling the distal displacement of the piston plunger 26 relative to said body 2. The said piston plunger 26 then drives the product 25 towards the needle 7 and the injection is administered, until the piston plunger 26 comes in abutment with the distal end of the body 2, as shown on FIG. 8.

Figure 9:
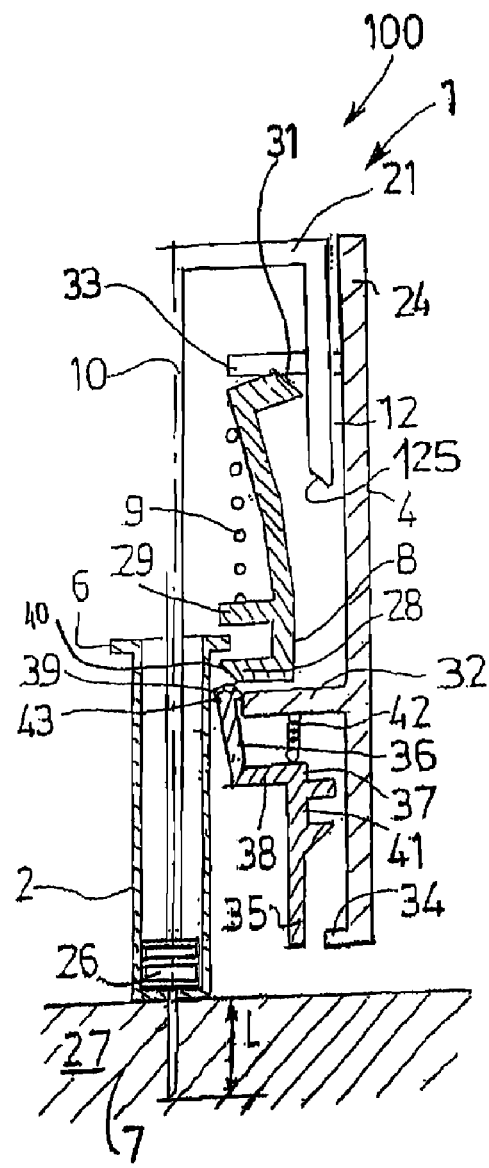

Once the injection is completed, under the effect of the axial pressure exerted on the said intermediate ring 8 by the said first spring 9, the said inclined distal face 40 of the said distal tooth 28 comes into abutment against the said sloping proximal face 39 of the said external radial step 43 and causes the inwards radial flexing of the said external radial step 43 which disengages the said sheath 35 from the said sleeve 4, as shown on FIG. 9.

Figure 10:
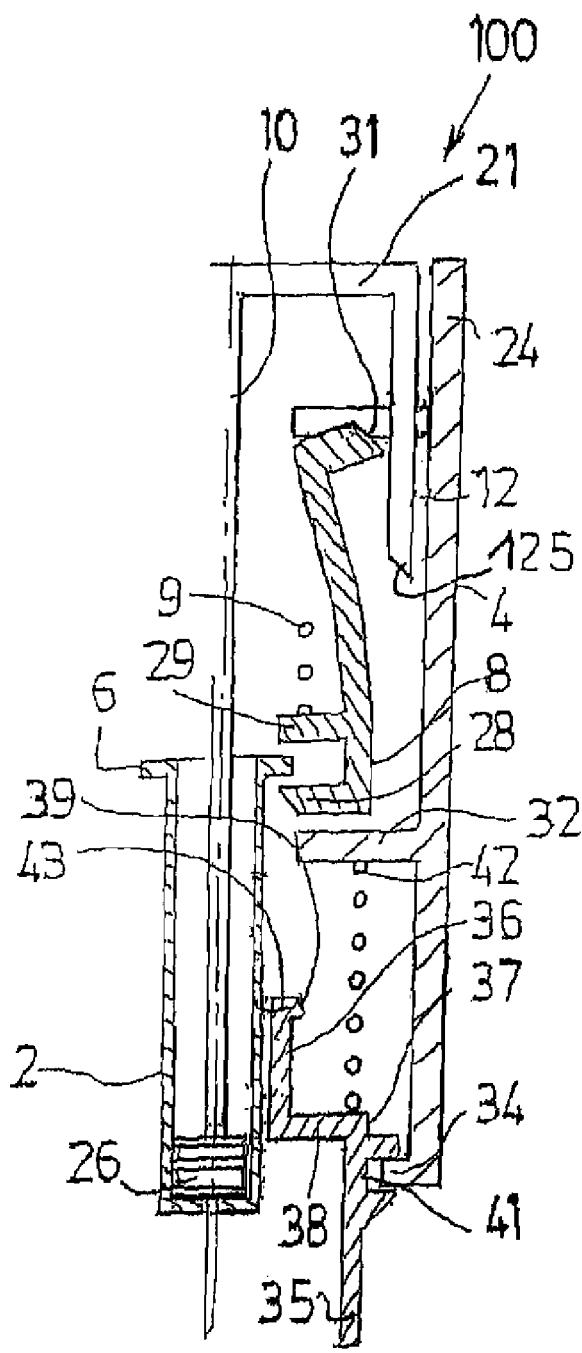

The user then withdraws the injection assistance device 1 from the surface of the injection site 27 and the second spring 42, relieved of the pressure exerted on it by the said surface of the said injection site 27 via the distal part 37 and the transverse wall 38 of the said sheath 35, returns to its expanded state, carrying with it the said sheath 35 which covers the needle 7 as shown in FIG. 10.

As the said second spring 42 deploys, the said bulge 34 of the said sleeve 4 is engaged in the said slot 41 of the said sheath 35, thus locking the translational movement of the said sleeve 4 with respect to the said sheath 35.

Thus, the injection assistance device 1 is completely safe and the user can discard it without the risk of needlestick injury.

FIGS. 11 to 14 depict a second alternative forms of embodiment of the injection set 100 according to the invention which also comprise automatic injection means.

FIGS. 11 to 14 relate to a first of its alternative forms. In these figures, the injection assistance device 1 according to the invention comprises a first spring 53 arranged between the said hollow body 2 and the said sleeve 4. The distal end 54 of the said first spring 53 is fixed to the internal wall of the distal part of the said sleeve 4. The proximal end 55 of the said first spring 53 bears against an inclined distal face 56 of the said head 21 of the plunger rod 10.

The sleeve 4 is provided on its internal walls with a radial stop 4a.

The injection assistance device 1 also comprises a second spring 57 arranged between the said head 21 of the plunger rod 10 and the distal face of the proximal region for holding 58 of the said sleeve 4.

Figure 12:
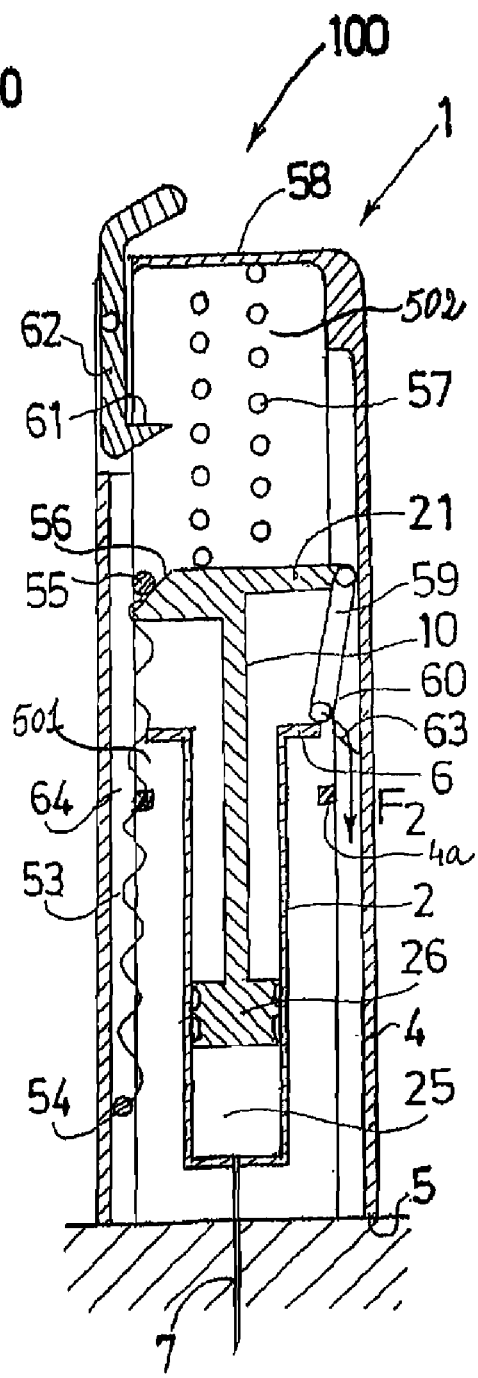
Figure 13:
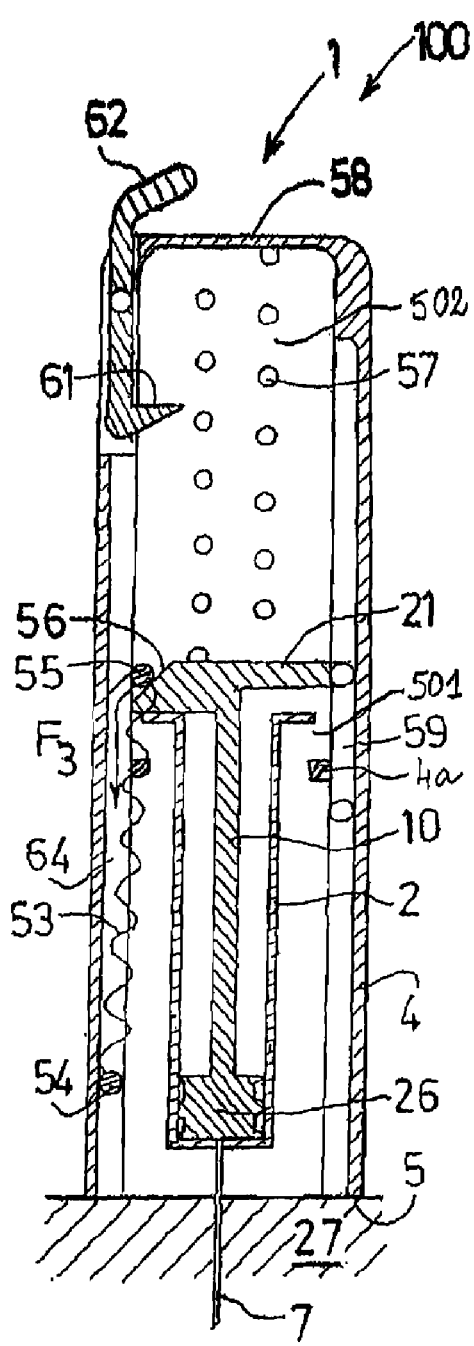

The head 21 of the plunger rod 10 comprises a longitudinal tab 59, extending in the distal direction, able to deflect outwards and engaging the said head 21 of the plunger rod 10 and the said flange 6, as depicted in FIG. 13. In FIGS. 11 to 14, this longitudinal tab 59 is in the form of an articulated arm comprising a window (not depicted) able to collaborate with a long bulge 60 formed on the proximal part of the internal wall of the said sleeve 4.

Figure 11:
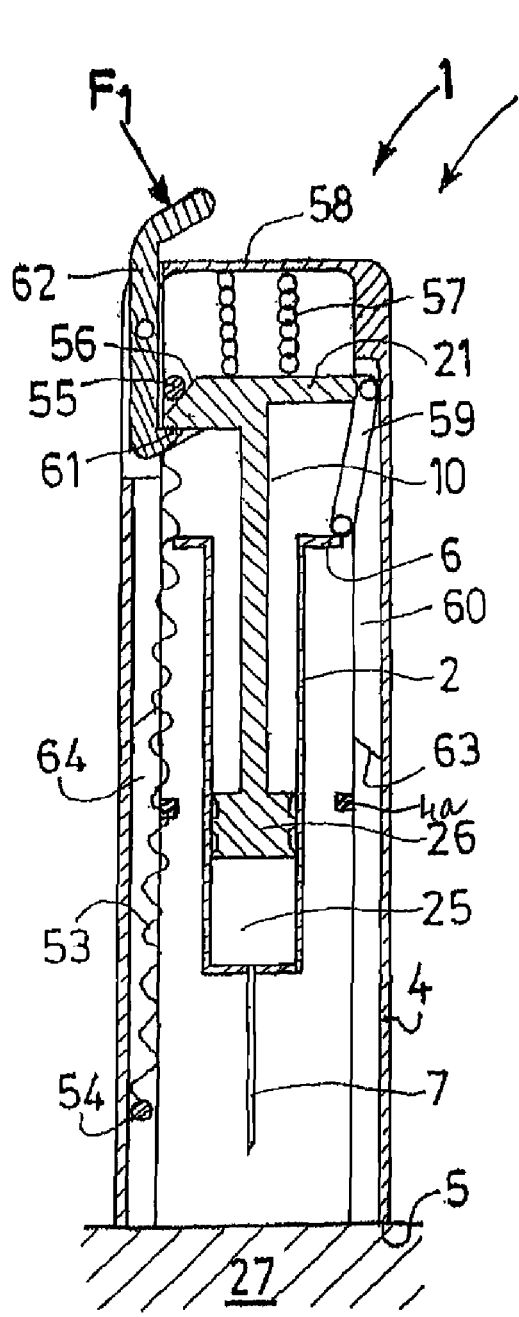

In the initial position, as depicted in FIG. 11, the said first spring 53 is in the stretched-out state. It is kept in this stretched-out state by a bearing surface 61 coupled to a button 62 situated on the external wall of the said sleeve 4, the said bearing surface 61 being able to deflect outwards and to release the said first spring 53 via pressure exerted on the said button 62.

The said second spring 52 is in the state of rest.

The plunger rod 10 is separated from the body 2 by an articulated arm 59 which, in the insertion step, as described below, will form spacer means preventing the plunger rod 10 from moving relative to said body 2.

Once the user has grasped the injection set 100 by the sleeve 4 and has brought said sleeve 4 to bear against the surface of the injection site 27, the user presses on the button 62 in the direction of the arrow F1 depicted in FIG. 11 to deflect the said bearing surface 61 and release the said first spring 53 which, on returning to a compressed state, drives the said head 21 of the plunger rod 10 in the distal direction. As the said head 21 of the plunger rod 10 is rigidly connected to the said flange 6 by the articulated arm 59, it is the assembly comprising the plunger rod 10 and the hollow body 2, and therefore the needle 7, which is moved in the distal direction, the said movement automatically inserting the said needle 7, as shown in FIG. 12.

During this movement, the said second spring 57, the distal end of which is fixed to the proximal face of the said head 21 of the plunger rod 10, has been stretched out, as shown in FIG. 12, and is therefore in a partially expanded state.

During the insertion step, the articulated arm 59 prevents the plunger rod 10 to move relative from the body 2. Therefore, there is no risk that the injection be started before the needle 7 is inserted at the right insertion depth L.

At the end of the insertion position, the said articulated arm 59 reaches the distal end 63 of the said bulge 60 and is deflected outwards, disengaging the said head 21 of the plunger rod 10 from the said flange 6, as shown by the arrow F2 in FIG. 12.

The said first spring 53 continues its return to its state of rest and carries with it the said head 21 of the plunger rod 10 which, free to move in the translational movement with respect to the said flange 6 and therefore with respect to the said hollow body 2, drives the said piston plunger 26 in the distal direction and administers the product 25. Thus, the injection is performed automatically without the user having to intervene.

During the injection step, the said second spring 57 is continued to be stretched out under the action of the said first spring 53.

As can be seen from FIGS. 12 and 13, a gap 501 is left between the flange of the body 2 and the radial stop 4a of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 57, because it is in a partially expanded state and thanks to the presence of the gap 501, is allowed to dampen said proximal movement by expanding a little more and thereby causing the head 21 of the plunger rod 10, and by consequence the body 2, to be urged towards the site injection 27. The needle 7 is therefore maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 57, because it is in a partially expanded state and thanks to the presence of the space 502 between the distal face of the proximal region for holding 58 of the sleeve 4 and the head 21 of the plunger rod 10, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 57 in a partially expanded state.

At the end of the injection position, as shown in FIG. 13, the proximal end 55 of the said first spring 53 disengaged from the inclined distal face 56 of the said head 21 of the plunger rod 10 in the direction of the arrow F3 because this head has arrived opposite a longitudinal depression 64 formed on the distal part of the internal wall of the said sleeve 4. The said first spring 53 therefore no longer exerts any tension on the said second spring 57 which returns to its compressed state of rest and carries with it the assembly comprising the head 21 of the plunger rod 10 and the hollow body 2, returning the said needle 7 to the inside of the said sleeve 4, as shown in FIG. 14.

Figure 14:
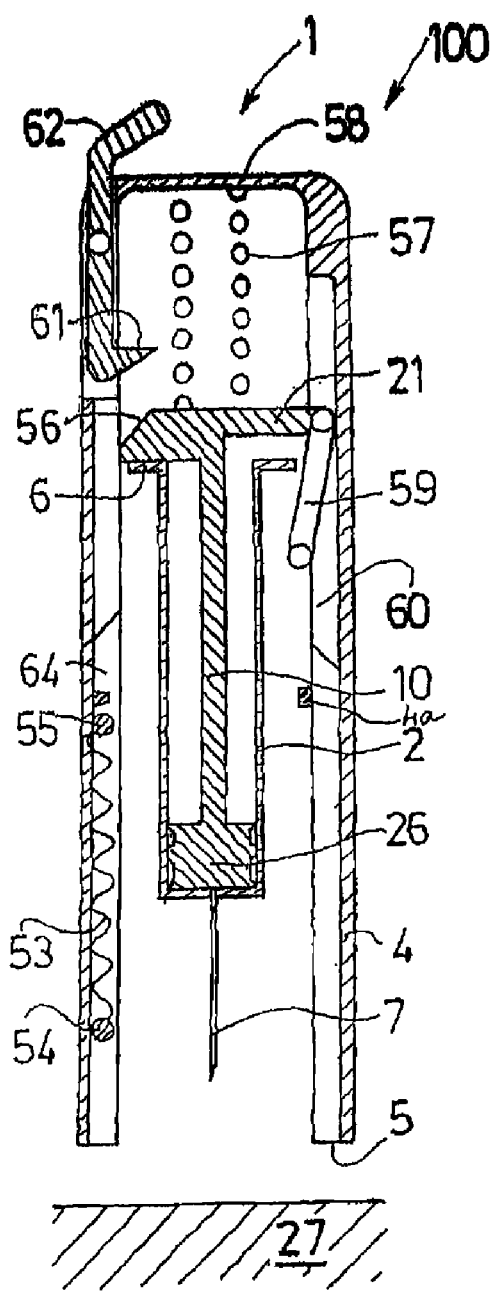

Thus, in the final protection position as depicted in FIG. 14, the said needle 7 is completely covered and the injection set 100 is safe. It can be discarded without any risk of needlestick injury to the user.

FIGS. 15 to 17 depict a third alternative form of embodiment of the injection set 100 according to the invention, of which the said sleeve 4 comprises a transverse wall 65 against the distal face of which the respective proximal ends of a first spring 66 and of a second spring 67 bear. The distal end of the said first spring 66 bears against the proximal face of the said flange 6. The distal end of the said second spring 67 bears against the said piston plunger 26.

The sleeve 4 is provided on its internal wall with a radial stop 94.

The plunger rod 10 is provided with a radial projection 10a.

The said injection assistance device 1 also comprises an intermediate ring 68, the proximal end of which comprises a first tab or laterally mobile tab 69 engaged in the said flange 6 in the initial position, said tab 69 being able to deflect in order to release the said flange 6 and therefore the said hollow body 2 through the collaboration of one 70 of its surfaces with a complementing surface 71 situated on a complementary rim 93 itself situated on the internal wall of the said sleeve 4. The tab 69 comprises a radial rim 69a.

In the initial position, as depicted in FIG. 15, the said first and second springs 66, 67 are in the compressed state, the said laterally mobile first tab 69 is engaged in the said flange 6.

The radial rim 69a of the tab 69 is engaged in the radial projection 10a of the plunger rod 10.

The user grasps the sleeve 4 of the injection assistance device 1 and applies it on the injection site 27. The user then presses on the proximal bearing region 58 to initiate the automatic insertion of the needle 7. This initiation takes place through the said surface 70 of the said deflecting first tab 71, coming into abutment against the said complementary surface 71 of the said sleeve 4 and subsequent deflection of the said tab 69 which releases at the same time the flange 6 and the radial projection 10a. The said first spring 66 is then free to return to a partially expanded state, carrying along with it the said flange 6 and therefore the said hollow body 2 and causes the needle 7 to become inserted into the injection site 27, as shown in FIG. 16.

Through deflection of tab 69, the radial rim 69a of said tab 69 has been disengaged from the radial projection 10a of the plunger rod 10, freeing said plunger rod 10. As the plunger rod 10 is not free to move before the body 2, the risk of inadvertent injection start before reaching the insertion depth L is limited.

The injection is performed automatically thanks to spring 67, without the user having to intervene.

As can be seen from FIGS. 16 and 17, a gap 601 is present between the flange 6 of the body 2 and the radial stop 94 of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 66, because it is in a partially expanded state and thanks to the presence of the gap 601, is allowed to dampen said proximal movement by expanding a little more and thereby causing the body 2, to be urged towards the injection site 27. The needle 7 is therefore maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 66, because it is in a partially expanded state and thanks to the presence of the space 602 between the distal face of the transversal wall 65 of the sleeve 4 and the body 2, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 66 in a partially expanded state.

FIGS. 18 to 29 relate to two alternative forms of embodiment of the injection set 100 according to the invention, in which forms the automatic-injection means are activated when the resultant of the forces of the said first and/or second and/or third return means, the force needed to overcome the stiction of the said piston plunger 26 and the force with which the sleeve 4 bears against the said injection site 27, is directed in the distal direction.

The injection assistance device 1 of FIGS. 18 to 22 comprises a sleeve tube 75 accommodating the said sleeve 4. The injection assistance device 1 also comprises a first spring 76 arranged between the said piston plunger 26 and the proximal face of the proximal region for holding 77 of the said sleeve tube 75. The said injection assistance device 1 also comprises a second spring 78 arranged between the said hollow body 2 and the said sleeve 4.

Figure 18:
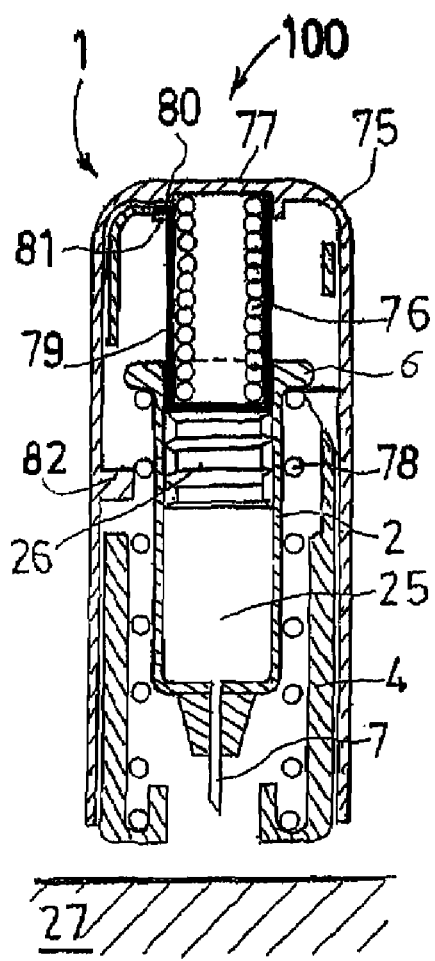

The said first spring 76 is housed within a casing 79, the distal end 80 of which bears, in the initial position as depicted in FIG. 18, against a deflecting tab 81 formed on the internal wall of the said sleeve tube 75. In the initial position, the said first spring 76 is in the compressed state and the said second spring 78 is in the expanded state.

The user grasps the sleeve tube 75 and applies the injection assistance device 1 on the injection site 27.

Figure 19:
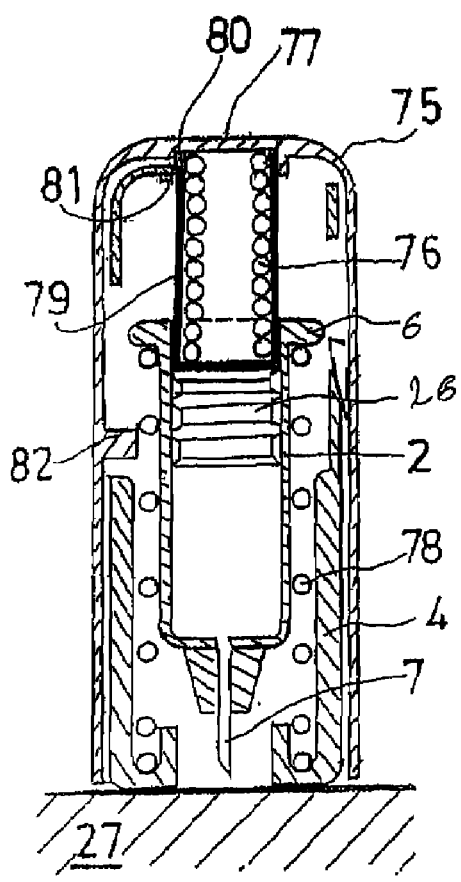

When the user presses against the said proximal region for holding 77 of the said sleeve tube 75, as shown in FIG. 19, the proximal end of the said sleeve 4 deflects the said tab 81 and disengages the said distal end 80 of the said casing 79 and thus releases the said first spring 76 which returns to a partially expanded state, carrying with it, at the same time, the said casing 79 and the said body 2, and causing the said needle 7 to be inserted automatically into the injection site 27, as shown in FIG. 20. While this is happening, the said second spring 78, the proximal end of which bears against the distal face of the said flange 6, is compressed.

As the plunger rod 10 is not free to move before the body 2, the risk of inadvertent injection start before reaching the insertion depth L is limited.

In the end-of-insertion position, the resultant of the forces of the said first and second springs 76, 78, the force needed to overcome the stiction of the said piston plunger 26 and the force with which the said sleeve 4 is pressed against the said injection site 27 is directed in the distal direction and so the said first spring 76 drives the said piston plunger 26 into the said hollow body 2 and perform the injection automatically, as shown in FIG. 21.

As can be seen on FIG. 20, a gap 701 is present between the flange 6 of the body 2 and a radial rim 82 formed on the internal wall of the said sleeve tube 75.

Therefore, if during the injection step, the user, for instance by inadvertence, releases the distal pressure he exerts on the sleeve tube 75 when applying it on the injection site 27, causing thereby a limited proximal movement of said sleeve tube 75, then the first spring 76, because it is in a partially expanded state and thanks to the presence of the gap 701, is allowed to dampen said proximal movement by expanding a little more and thereby causing the body 2, to be urged towards the site injection 27. The needle 7 is therefore maintained at a constant insertion length, namely its predetermined insertion length L.

On the contrary, if during the injection step, the user increases the distal pressure he exerts on the sleeve tube 75 when applying it on the injection site 27, causing thereby a limited distal movement of said sleeve tube 75, then the first spring 76, because it is in a partially expanded state and thanks to the presence of the space 702 between the distal face of the proximal region for holding 77 of the sleeve tube 75 and the piston plunger 26, is allowed to dampen said distal movement by being compressed, thereby maintaining the needle 7 at a constant insertion length, namely its predetermined insertion length L.

The influence of any increase or release of the distal pressure exerted by the user on the sleeve tube 75 during injection step is therefore neutralized by the presence of the spring 76 in a partially expanded state.

At the end of injection, the user withdraws the injection set 100 from the injection site 27 and the said second spring 78, on returning to its expanded state, drives the said sleeve 4 in the distal direction and the needle 7 is covered up again, as shown in FIG. 22. The injection set 100 is therefore completely safe.

The injection sets and the injection assistance devices according to the invention are particularly simple to use and are perfectly safe. The entire injection operation can easily be performed by a single unidirectional axial movement, with just one hand. Moreover, the device of the invention ensures a two step use, with a first step for the insertion, and a second step for the injection. There is therefore little risk to start the injection before reaching the right insertion depth. In addition, the devices ensure a predetermined stable insertion depth during the injection step even despites slight movement of the user's hand.

The invention claimed is:

1. Injection assistance device (1) for an injection device (3) for injecting a product (25) into an injection site (27), this injection device (3) comprising at least one hollow body (2) intended to receive a product (25) that is to be injected, at least one hollow injection needle (7) intended to penetrate the injection site (27), and at least one piston plunger (26) housed in the said body (2), the said body (2) and the said piston plunger (26) being able to be moved in axial translation one with respect to the other, characterized in that the said injection assistance device (1) comprises at least:

a hollow sleeve (4) provided with at least one bearing surface (5) intended to come into contact with the surface of the said injection site (27), the said sleeve (4) being intended to receive, at least in part, the said body (2) and being arranged in such a way as to allow the said body (2) axial mobility between at least a first position known as the initial position in which the said needle (7) is covered by the said hollow sleeve (4) so as to be not exposed over its insertion length, and a second position known as the insertion position in which the said needle (7) extends beyond the said hollow sleeve (4) so as to be exposed by a predetermined insertion length L, a coupling (10, 76) arranged in such a way as to be coupled to said piston plunger (26) at least during an injection step so as to move said piston plunger (26) from an end-of-insertion position to an end of injection position and to administer the injection when submitted to a distal pressure exerted thereon, a spacer (8; 30; 59; 69; 81, 80) arranged in such a way as to maintain at least said piston plunger (26) and said body (2) in said initial position, a disengager (22, 14, 15, 16; 25, 31; 61; 70, 71; 4) linked with said spacer (8; 30; 59; 69; 81, 80), said spacer (8; 30; 59; 69; 81, 80) and disengager (22, 14, 15, 16; 25, 31; 61; 70, 71; 4) being arranged in order to free distal displacement of said piston plunger (26) only after distal displacement of said body (2), with the said body (2) comprising a flange (6) at its proximal end, the said spacer comprises at least one deflecting tab (59) engaging the said flange (6) and the said coupling (10) in the insertion position so as to inhibit distal movement of the said coupling (10) relative to the said body (2), the said tab (59) deflecting to disengage from the said flange (6) at the end of the insertion position with the said needle (7) being exposed by the predetermined insertion length L so as to allow the said coupling (10) to move distally relative to the said body (2).

2. Injection assistance device (1) according to claim 1, characterized in that it further comprises:
an automatic inserter (9; 49; 53; 66; 76) arranged in such a way as to cause the said body (2) to move axially in the distal direction and to insert the said hollow needle (7) into the injection site (27),
a retainer (14, 15, 18; 12, 125, 30, 31; 44, 45; 48, 49; 61, 62; 69, 70, 71; 77, 76) for retaining the said body (2) in the said initial position, the said automatic inserter (9; 49; 53; 66; 76) being activated by the release of the said retainer (14, 15, 18; 12, 125, 30, 31; 44, 45; 48, 49; 61, 62; 69, 70, 71; 77, 76).

3. Injection assistance device (1) according to claim 2, characterized in that the said coupling comprises at least one plunger rod (10) detached from the said piston plunger (26), the said plunger rod (10) being able, once coupled to said piston plunger (26), to drive the said piston plunger (26) in the distal direction when urged in the distal direction.

4. Injection assistance device (1) according to claim 2, characterized in that the said automatic inserter comprises third elastic return means (9; 49; 53; 66; 76) connected to the said sleeve (4) and intended to urge the said body (2) from the initial position to the said insertion position.

5. Injection assistance device (1) according to claim 1, characterized in that said spacer forming a substantially rigid link between said body (2) and said piston plunger (26) and preventing their relative displacement before the triggering of said disengager (22, 14, 15, 16; 25, 31; 61).

6. Injection assistance device (1) according to claim 5, characterized in that said disengager (22, 14, 15, 16; 25, 31; 61) is arranged in order to automatically disengage said spacer (8; 30; 59; 69) when the insertion position is reached and free the relative displacement of said piston plunger (26) and said body (2).

7. Injection assistance device (1) according to claim 1, characterized in that it further comprises an automatic injecter (53; 67; 76) arranged in such a way as to urge the said coupling (10, 76) at the end of the insertion position without manual intervention on the part of the user.

8. Injection assistance device (1) according to claim 7, characterized in that the said automatic injecter comprises first return means (53; 67; 76) connected to the said coupling (10) and intended to urge the said coupling (10) from the insertion position to the said end-of-injection position.

9. Injection assistance device (1) according to claim 7, characterized in that the said automatic injecter (53; 67; 76) being activated by the release of the said spacer (59; 10a, 69a).

10. Injection assistance device (1) according to claim 9, characterized in that triggering said disengager (22, 14, 15, 16; 25, 31; 61) simultaneously performs the disengagement of said spacer (8; 30; 59; 69) and the activation of said automatic injecter (53; 67; 76).

11. Injection assistance device (1) according to claim 1, characterized in that it further comprises a final protector (4; 8; 35, 37) arranged in such a way as to cover the said needle (7) in a post-injection final protection position, wherein said final protector is able to move in translation with respect to the said body (2) between an injection position in which the needle (7) is exposed and a final protection position in which the needle (7) is covered.

12. Injection assistance device (1) according to claim 11, characterized in that the final protector is chosen from the said sleeve (4) and an intermediate sheath (8; 35, 37) arranged between the said sleeve (4) and the said body (2).

13. Injection assistance device (1) according to claim 11, characterized in that it comprises an automatic activator (9; 42; 50; 57; 78) for activating the said final protector (4; 8; 35) at the end of injection.

14. Injection assistance device (1) according to claim 13, characterized in that the automatic activator comprises second return means (9; 42; 50; 57; 78) connected to the said final protector (4; 8; 35) intended to urge the said body (2) from the said injection position to the said final protection position.

15. Injection assistance device (1) according to claim 11, characterized in that it comprises a lock (17; 34, 41; 52) arranged in such a way as to at least limit the translational movement of the said body (2) with respect to the said final protector (4; 8; 35) in the final protection position.

16. Injection assistance device (1) according to claim 1, characterized in that it comprises a controller (19; 32; 59; 82; 91; 94) arranged in such a way as to delimit the said insertion position of the said body (2).

17. Injection assistance device (1) according to claim 16, characterized in that the said controller comprises at least one radial stop (19; 32; 94; 91) provided in the said sleeve (4) and intended to have the said body (2) bearing against it.

18. Injection assistance device (1) according to claim 16, characterized in that with the said piston plunger (26) connected to a plunger rod (10) intended to urge the said piston plunger (26) in the distal direction in order to perform the injection, the said controller comprises a blocker (59) for blocking the translational movement of the said plunger rod with respect to the said piston plunger, the said blocker being able to be released when the said body (2) is at the end of the insertion position, the said needle (7) being exposed by the said predetermined insertion length L.

19. Injection set (100) for injecting a product (25) into an injection site, the said injection set (100) comprising at least:
an injection device (3) comprising at least:
a hollow body (2) intended to receive a product (25) that is to be injected, the said body (2) being equipped with a hollow injection needle (7) intended, during a first step known as the insertion step, to penetrate an injection site (27) and, during a second step known as the injection step, to channel the said product (25) from the said body (2) towards the said injection site (27),
at least one piston plunger (26) housed in a more or less sealed manner in the said body (2) and intended to be moved in the distal direction by movement means in the said injection step during which it drives the said product (25) through the said needle (7),
characterized in that it comprises at least an injection assistance device (1) for assisting with the injection device (3) according at least to claim 1.

20. Injection set (100) according to 19, characterized in that it is in the form of a kit that can be assembled prior to use.

* * * * *